US012491102B2

(12) United States Patent
Lurssen et al.

(10) Patent No.: US 12,491,102 B2
(45) **Date of Patent: *Dec. 9, 2025**

(54) ORTHOSIS JOINT

(71) Applicant: OTTOBOCK SE & CO. KGAA, Duderstadt (DE)

(72) Inventors: Marcus Lurssen, Gottingen (DE); David Hochmann, Steinfurt (DE); Roland Auberger, Vienna (AT); Gordon Siewert, Gottingen (DE); Christian Breuer-Ruesch, Vienna (AT)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 1302 days.

This patent is subject to a terminal disclaimer.

(21) Appl. No.: 16/783,601

(22) Filed: Feb. 6, 2020

(65) Prior Publication Data

US 2020/0170821 A1 Jun. 4, 2020

Related U.S. Application Data

(63) Continuation of application No. 14/903,986, filed as application No. PCT/EP2014/001877 on Jul. 8, 2014, now Pat. No. 10,555,829.

(30) Foreign Application Priority Data

Jul. 9, 2013 (DE) ......................... 102013011382.2

(51) Int. Cl.
*A61F 5/00* (2006.01)
*A61F 5/01* (2006.01)

(52) U.S. Cl.
CPC .......... *A61F 5/0127* (2013.01); *A61F 5/0125* (2013.01); *A61F 2005/0165* (2013.01);
(Continued)

(58) Field of Classification Search
CPC .... A61F 5/0123; A61F 5/0125; A61F 5/0127; A61F 5/013; A61F 2005/0137;
(Continued)

(56) References Cited

U.S. PATENT DOCUMENTS 4,489,718 A 12/1984 Martin
4,727,861 A 3/1988 Yeomans et al.
(Continued)

FOREIGN PATENT DOCUMENTS

DE 102010014334 A1 10/2011
RU 2092136 C1 10/1997
UA 87226 C2 6/2009

OTHER PUBLICATIONS

PCT International Search Report for PCT International Patent Application No. PCT/EP2014/001877, mailed Oct. 29, 2014.

*Primary Examiner* — Adam Baker
(74) *Attorney, Agent, or Firm* — HOLLAND & HART LLP

(57) ABSTRACT

An orthosis joint having a base body which comprises a receptacle for a proximal component, a bearing point for a distal component which is pivotally arranged on the base body, and for stops or spring elements which are acting on the distal component. The orthosis joint also includes at least one receiving element releasably fastened to the base body and in or on which a functional element that interacts with the distal component is arranged.

19 Claims, 9 Drawing Sheets

(52) U.S. Cl.
CPC ................. *A61F 2005/0167* (2013.01); *A61F 2005/0169* (2013.01); *A61F 2005/0179* (2013.01)

(58) Field of Classification Search
CPC ...... A61F 2005/0139; A61F 2005/0155; A61F 2005/0158; A61F 2005/0162; A61F 2005/0165; A61F 2005/0167; A61F 2005/0169; A61F 2005/0179; A61F 2005/0188; A61F 2005/0197
USPC .............................................................. 602/16
See application file for complete search history.

(56) References Cited

U.S. PATENT DOCUMENTS

| | | | | | |
|---|---|---|---|---|---|
| 4,771,768 | A * | 9/1988 | Crispin | A61F 5/0127 | D24/190 |
| 4,928,676 | A * | 5/1990 | Pansiera | A61F 5/0125 | 602/16 |
| 5,052,379 | A * | 10/1991 | Airy | A61F 5/0125 | 482/901 |
| 5,328,444 | A * | 7/1994 | Whiteside | A61F 5/0127 | 16/375 |
| 5,372,574 | A | 12/1994 | Hino et al. | | |
| 5,376,134 | A | 12/1994 | Biedermann | | |
| 5,399,149 | A * | 3/1995 | Frankowiak | A61F 5/0125 | 403/322.2 |
| 5,899,869 | A | 5/1999 | Barrack, Jr. et al. | | |
| 6,080,123 | A | 6/2000 | Pansiera | | |
| 6,969,365 | B2 | 11/2005 | Scorvo | | |
| 8,066,653 | B2 | 11/2011 | Seon | | |
| 8,435,309 | B2 | 5/2013 | Gilbert et al. | | |
| 2007/0010772 | A1 | 1/2007 | Ryan | | |
| 2008/0039756 | A1 | 2/2008 | Thorsteinsson | | |
| 2011/0251539 | A1* | 10/2011 | Gentz | B26D 7/08 | 602/16 |
| 2012/0232438 | A1 | 9/2012 | Cataldi et al. | | |

* cited by examiner

A-A

ORTHOSIS JOINT

CROSS-REFERENCE TO RELATED APPLICATIONS

This is a continuation application of U.S. patent application Ser. No. 14/903,986, filed 8 Jan. 2016, issued 11 Feb. 2020 as U.S. Pat. No. 10,555,829, and entitled ORTHOSIS JOINT, which is a U.S. National Entry Application from PCT International Patent Application No. PCT/EP2014/001877, filed 8 Jul. 2014, and also entitled ORTHOSIS JOINT, which claims the benefit of German Patent Application No. 102013011382.2, filed 9 Jul. 2013.

TECHNICAL FIELD

The invention relates to an orthosis joint having a base body which comprises a receptacle for a proximal component, a bearing point for a distal component arranged pivotably on the base body, and limit stops or spring elements which act on the distal component. An orthosis joint of this kind can advantageously be used in particular on orthoses of lower extremities, such as an ankle-foot orthosis (AFO) or a knee-ankle-foot orthosis (KAFO), but it is not limited to this intended use.

BACKGROUND

Orthoses serve to support the movement of natural limbs or to stabilize the latter. For this purpose, support structures in the form of shells or rails are generally provided which are secured to the limbs. Except in the case of immobilization orthoses, joints are provided between the support devices in the area of the natural joints and permit relative movement. The movement can be limited in terms of its direction or in terms of its extent if this is deemed useful from the therapeutic point of view. In addition, the movement can be opposed by a resistance, or restoring forces can be applied such that a return to an initial position takes place or is at least facilitated.

DE 10 2010 014 334 A1 relates to an orthosis joint with two functional means for forming two limit stops. The functional means are designed as a cup spring arrangement and are arranged in spring channels. The spring channels are formed in the base body and act on a stirrup arranged pivotably on the base body. The pretensioning of the cup spring arrangement can be modified via an adjusting element that is screwed into the spring channel.

U.S. Pat. No. 4,489,718 relates to a knee orthosis joint via which the maximum attainable knee angle can be adjusted. A continuous channel is arranged in a base body, in which continuous channel two springs are arranged which engage on a pin of a pivot part mounted in an articulated manner on the base body. By modifying the pretensioning of the springs by way of two adjustment elements that can be screwed in, it is possible to adjust the maximum attainable knee angle both in the direction of flexion and also in the direction of extension.

U.S. Pat. No. 4,771,768 relates to an ankle orthosis for treatment of ankle fractures. A foot part is secured in an articulated manner on a below-knee rail. A base body is arranged on the below-knee rail, in which base body two metal pins are inserted that can be moved toward or away from projections on the foot part via adjustment screws. The extent of movement and the maximum attainable ankle angle can be adjusted via these metal pins.

A problem of the prosthesis joints known from the prior art is the fact that they are designed specifically for their respective intended use. It is not possible, or it is possible only with considerable effort, to individually tailor the orthosis joint and adapt it to the specific user and, if appropriate, to any progress that is made in therapy.

SUMMARY

The object of the present invention is to make available an orthosis joint that can be easily tailored to the individual.

According to the invention, this object is achieved by an orthosis joint having the features of the main claim. Advantageous embodiments and developments of the invention are set forth in the dependent claims, the description and the figures.

In the orthosis joint according to the invention having a base body which comprises a receptacle for a proximal component, a bearing point for a distal component arranged pivotably on the base body, and limit stops or spring elements which act on the distal component, provision is made that at least one receiving element, in or on which a functional element interacting with the distal component is arranged, is releasably secured to the base body. Whereas in orthosis joints from the prior art the limit stops or spring elements arranged therein are received completely in the base body and are guided therein, provision is made according to the invention that a receiving element for a functional element is secured releasably on the base body, such that the receiving element is exchangeable and adaptable to the individual requirements of the user. It is thereby possible for different functional elements or also different configurations of one functional element, for example of a spring, to be received or guided in the receiving element, so as to permit easy adaptation to the particular requirements.

The receiving element is advantageously reversibly secured with a form fit to the base body for example via a thread, which is provided correspondingly on the receiving element and on the base body. It is likewise possible to secure the receiving element via a bayonet catch or clips, resilient locking tabs or other form-fit elements.

The receiving element can be designed as a sleeve with a thread in order on the one hand to secure the receiving element on the base body or on the other hand to position and adjust the functional element inside the receiving element.

The functional element can be designed as a spring, spring assembly, damper, sensor or limit stop, or a combination of these. The respective receiving element is adapted in form and presentation to the respective functional element; if dampers, springs or spring assemblies are used, the receiving element serves as an external guide for the damper, the spring or the spring assembly. If sensors are used as functional elements, the sensor housing is the receiving element and optionally has interfaces for forwarding sensor data and securing devices for securing it to the base body. Limit stops that define the range of movement in the joint can likewise be arranged in the receiving element. For the adjustable positioning of the respective limit stops, provision is made that adjustment devices are provided on the receiving element, so as to be able to carry out adaptation without having to exchange the limit stop itself.

Several functional elements can be arranged one behind another in series, in order to combine different functions. For example, a spring and a sensor can be arranged in series in order, as a module, to supply information concerning the applied force or the displacement path. Similarly, serial spring-damper combinations can be used, or springs with different levels of stiffness can be arranged one after another in order to achieve a progressive characteristic curve.

The functional element can be designed as an inductive sensor, which detects a displacement path permitted, for example, by springs, spring assemblies or dampers, such that the displacement path and/or an angle setting can be determined via the inductive sensor.

The receiving elements and the functional elements can be designed as an integrated assembly or integrated function module, such that a modular structure of the orthosis joint can be easily obtained. Functional elements are integrated in the respective receiving element or are pre-installed, such that an adaptation and individualization of the orthosis joint can be easily effected by exchange of the functionalized receiving elements.

Several receiving elements can be arranged one after another in series, for example by a screw connection or other form-fit elements such as a bayonet catch or locking connections. For this purpose, corresponding screws or form-fit elements are provided on the receiving elements that are intended to be coupled to each other, such that an outer thread can be screwed into an inner thread or the corresponding form-fit elements can be locked onto each other, in order either to lengthen the receiving elements for a correspondingly large functional element or to permit a combination of different functional elements with each other. For example, instead of having to keep a stock of several receiving elements in the form of channels with the respectively correct length, it is possible for several short receiving elements to be combined with each other to form a receiving element or a channel of the desired length.

The receiving element is advantageously inserted in a recess in the base body, in which recess form-fit elements for securing the receiving element are arranged. The form-fit elements can be designed as threads, a guide track for bayonet catches, resilient tongues, projections or the like. From the recess, a channel leads in the direction of the distal component in order to establish an operative connection to the distal component, for example a shoulder of a joint part. Pins, bolts or other pressure elements can be guided through the channel in order to convey forces from the distal component to the functional element. It is likewise possible that the functional element acts directly on the distal component through the channel, for example by springs bearing directly on support surfaces of the distal component or by a limit stop striking a support surface when the maximum angle setting is reached. It is also possible that a sensor detects the position of the distal component relative to the base body through the channel or takes up the forces acting on the distal component. It is thereby possible, for example, to use the joint in a controlled orthosis and to obtain, by way of the sensors, information that is wanted concerning the state of movement, the nature of the movement and the like.

The receptacle on the base body can be designed as a rail box in which an orthosis rail, for example for a below-knee part or an upper leg part, is secured. It can be secured by clamping and/or by a form-fit engagement, for example via a double screw connection and conically tapering side walls on the rails and/or on the rail box.

The distal component can be designed as a rail, rail box, shell, foot stirrup or foot support. A foot support is understood as meaning components that engage under the foot, while foot stirrups are components that can also extend parallel to the foot; foot stirrups can end in a foot support.

The receiving elements are advantageously arranged on both sides of the bearing point, such that the functional elements can be arranged efficiently both in terms of flexion and also extension.

The receiving element can protrude beyond the contour of the base body such that, when the receiving element is not secured on the base body, it is possible to obtain a slim design of the base body and, therefore, of the whole orthosis.

BRIEF DESCRIPTION OF THE DRAWINGS

Illustrative embodiments of the invention are explained in more detail below with reference to the attached figures, in which:

FIG. 6 shows a variant of FIG. 1, with a limit stop channel screwed in;

FIG. 12 shows a variant of FIG. 10, with spring receptacles screwed in;

FIG. 14 shows a perspective view of a base body with a sensor screwed in;

DETAILED DESCRIPTION

Figure 1:
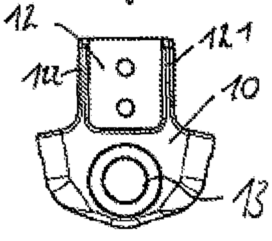

FIG. 1 is a plan view showing a base body 10 of an orthosis joint with a receptacle 12 for a proximal component (not shown), for example an orthosis rail, and also a bearing point 13 for receiving a pivot shaft on which a distal component (not shown) can be pivotably secured to rotate about a pivot axis.

Figure 2:
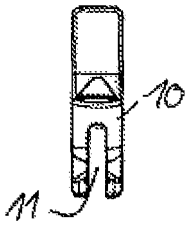

FIG. 2 shows the base body 10 in a view turned to the right. It will be seen that a slit 11 is formed in the base body 10, which slit 11 serves to receive the distal component. The webs of the base body 10, which are arranged on both sides of the slit 11, each have the through-bore for the pivot shaft and form the bearing point 13 for the distal component.

Figure 3:
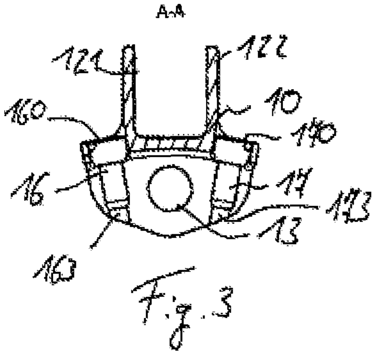

FIG. 3 shows the base body 10 in a sectional view with the bearing point 13 and with the two upwardly directed arms of the lateral walls 121, 122 of the receptacle 12. The receptacle 12 is designed as a trough-shaped rail box and, on the bottom wall cut away, has recesses through which form-fit elements, for example screws, can be guided in order to secure an orthosis rail to the base body 10.

On both sides of the bearing point 13, recesses 16, 17 in the form of bores are present which, at the proximal end, have form-fit elements 160, 170 that can be designed as inner threads or locking elements for a bayonet catch. Alternatively to this, the form-fit elements 160, 170 can be designed as resiliently mounted locking units. At the distal end of the recesses 16, 17 lying opposite the form-fit elements 160, 170, channels 163, 173 are provided which point in the distal direction, such that a free passage extends from the proximal side of the base body 10 to the distal side of the base body 10 and thus to the distal component (not shown).

Figure 5:
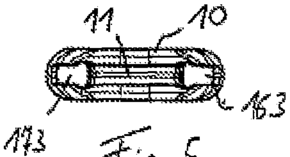
FIGS. 1-5 show various views of a base body without receiving elements.
Figure 4:
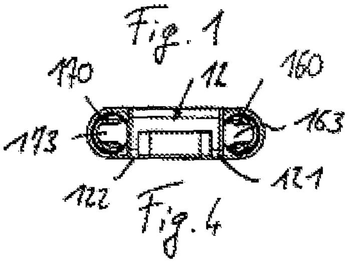

The free passages on both sides of the bearing point 13 can be seen as channels 163, 173 in FIGS. 4 and 5. FIG. 4 also reveals the box-shaped design of the receptacle 12 with the bottom wall and the two forwardly protruding walls 121, 122. FIG. 4 likewise shows the form-fit elements 160, 170 in the form of threads. FIG. 5 shows the continuous channels 163, 173, and likewise the slit 11 on the distal portion of the base body 10.

Figure 6:
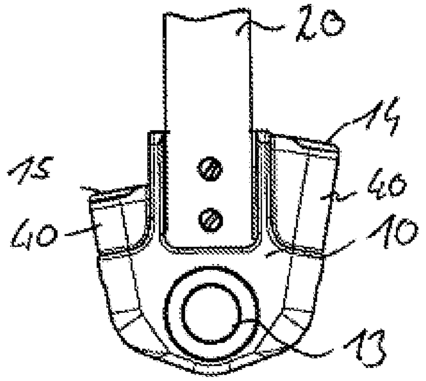

In FIG. 6, the base body 10 of the joint is shown with a fitted proximal component 20 in the form of an orthosis rail. The orthosis rail 20 is secured to the base body 10 via screws. In the view in FIG. 6, two receiving elements 14, 15 are secured to the base body 10 on both sides of the proximal component 20. Cladding parts 40 are arranged around the receiving elements 14, 15 in order to allow the orthosis joint to have the smoothest possible walls and a compact structure.

Figure 7:
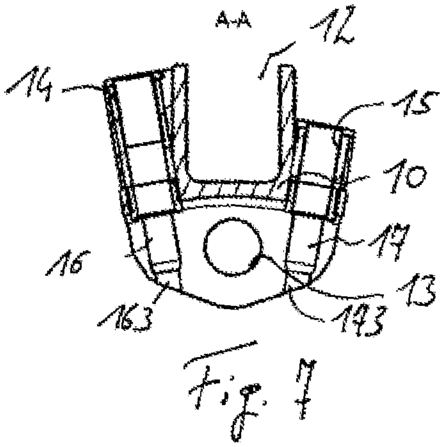
FIG. 7 shows a sectional view of FIG. 6.

In FIG. 7, the base body 10 according to FIG. 6 is shown in a rotated sectional view. Here too, the two recesses 16, 17 arranged symmetrically on both sides of the bearing point 13 can be seen, which recesses 16, 17 open into the channels 163, 173. The receiving elements 14, 15 are screwed into the threads 160, 170, as shown in FIG. 3. By means of the receiving elements 14, 15 being screwed in, the two claddings 40 are also fixed on the base body.

Figure 8:
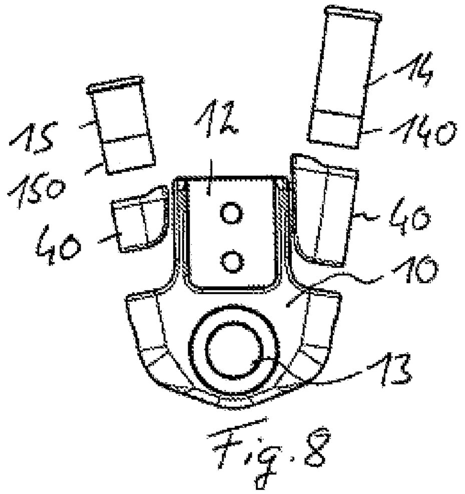
FIG. 8 shows an exploded view of FIG. 6.

FIG. 8 shows the variant of FIG. 6 in an exploded view. It will be seen that the claddings 40 have a configuration matching the contour of the base body 10, such that the claddings 40 supplement the outer contour. As a result of the symmetrical structure, it is possible for the two receiving elements 14, 15 of different length to be secured either in the left-hand or the right-hand recess 16, 17. In order to secure the receiving elements 14, 15, the receiving elements designed as sleeves are screwed into the threads 160, 170. For this purpose, outer threads 140, 150 are arranged on the distal ends of the receiving elements 14, 15. Shoulders are arranged on the proximal ends and are designed such that they bear on the upper edges of the claddings 40, with the result that the claddings 40 are secured on the base body 10 as the receiving elements 14, 15 are screwed in.

Figure 9:
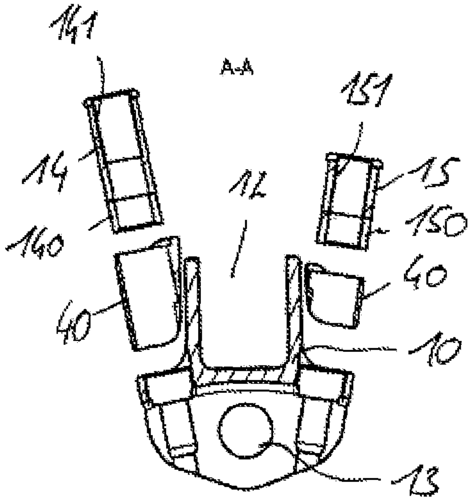
FIG. 9 shows FIG. 8 in a sectional view.

FIG. 9 shows FIG. 8 in a sectional view. It will be seen that the sleeve-shaped receiving elements 14, 15 have outer threads 140, 150 at the distal end. In addition, the receiving elements 14, 15 are provided with inner threads 141, 151 such that functional elements (not shown) arranged in the receiving elements 14, 15 are fixed therein and, if appropriate, can be pretensioned in the direction of the distal component. The claddings 40 have through-openings, as do the receiving elements 14, 15, such that a continuous and direct connection is present from the upper edge of the receiving elements 14, 15 to the opening of the channels 163, 173. On account of the symmetrical configuration both of the base body 12 and also of the claddings 40, it is possible to secure the respective receiving elements 14, 15 on one of the two recesses 16, 17 and to use the orthosis joint both to the left and also to the right. In the illustrative embodiment shown, the shorter receiving element 15 is provided to receive a limit stop, while the longer receiving element 14 is provided to receive a spring assembly.

Figure 10:
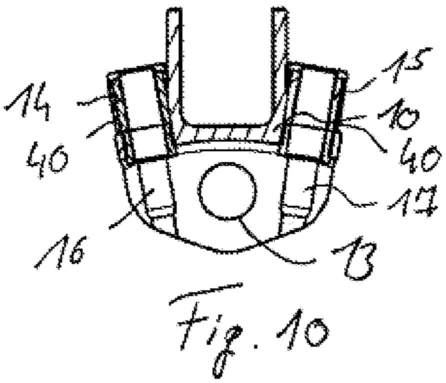
FIG. 10 shows a sectional view according to FIG. 7, with receiving elements screwed in on both sides.
Figure 11:
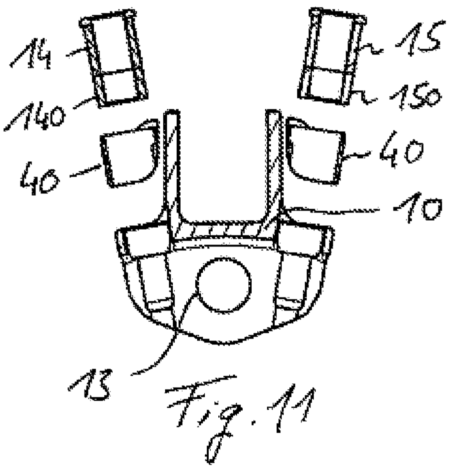
FIG. 11 shows an exploded view of FIG. 10.

FIGS. 10 and 11 show variants of FIGS. 7 and 9, in which, instead of a long receiving element 14 serving as a spring channel, two receiving elements 14, 15 of equal length and in the form of sleeves are screwed into the base body 10. Both receiving elements 14, 15 serve in the present case as a limit stop channel.

Figure 12:
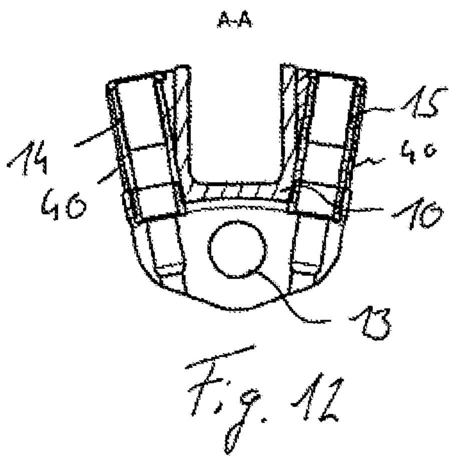
Figure 13:
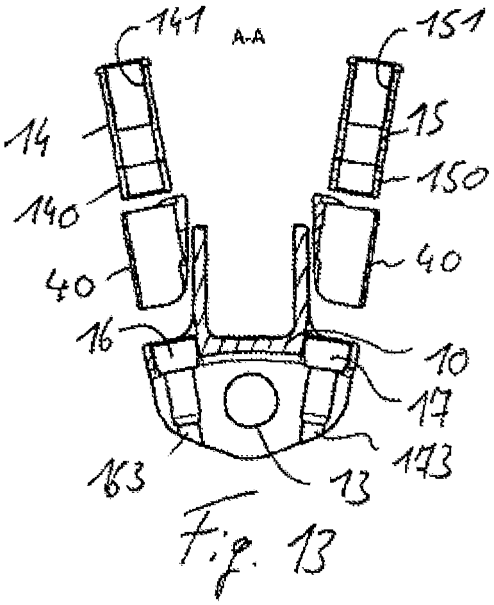
FIG. 13 shows a sectional view of FIG. 12.

FIGS. 12 and 13 show a variant of the invention in which, instead of two limit stops being screwed in as shown in FIGS. 10 and 11, two spring channels serving as receiving elements 14, 15 are screwed into the recesses 16, 17 on both sides of the bearing point 13.

Figure 14:
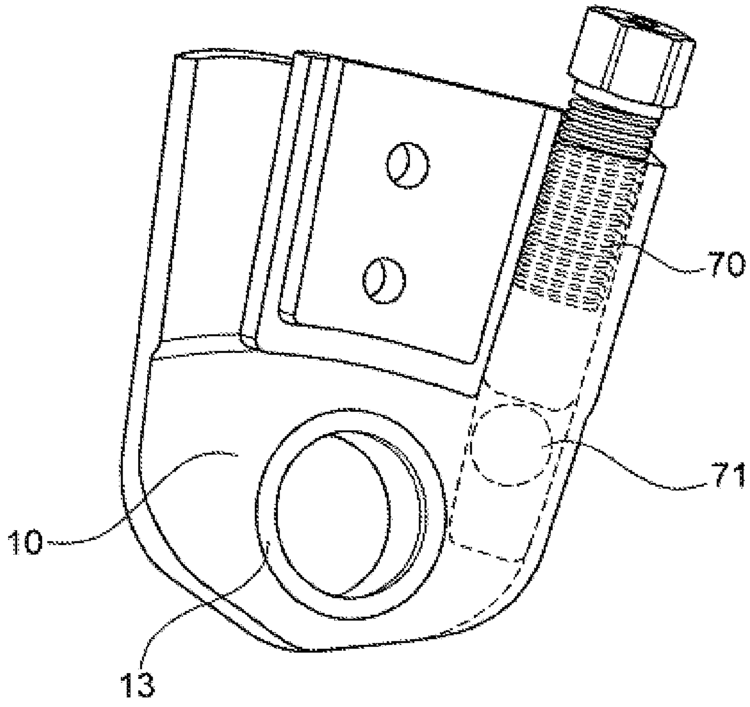

FIG. 14 shows a further variant of the invention in which, in the base body 10, a sensor 70 serving as a functional element is screwed into a recess 16. The sensor housing serves here as receiving element and has an outer thread, which is screwed into the inner thread 160 of the receptacle 16. At the distal end of the sensor 70, a ball 71 is arranged as a contact element which takes up forces from the distal component (not shown) and transmits them to the actual sensor element, which is designed for example as a pressure sensor and has a piezoresistive or capacitive action. Alternatively, the functional element 70 can be affixed to a strain gauge in order to determine whether and with what force the distal component 30 presses against the ball 71. In principle, it is also possible for sensors 70 to be installed as functional elements on both sides, so as to record sensor data in each loading direction, in the case of an orthosis joint that is pivotable to both sides from an initial position. In the case of a KAFO or AFO, it is possible in addition to detect a ground contact, the strength of the ground contact, and also a toe-off.

Figures 15, 16, 17, 18, 19, 20, 21:
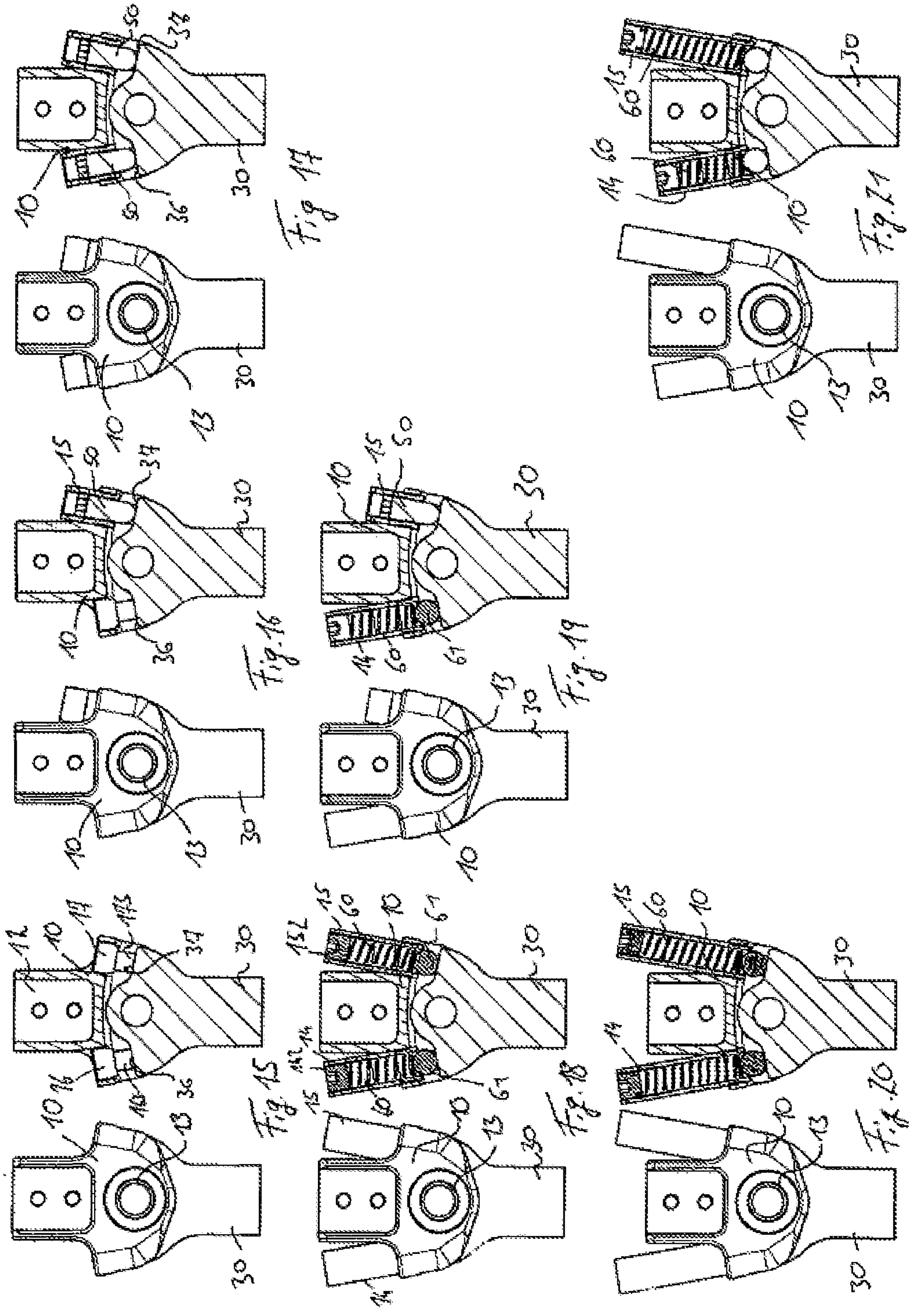
FIGS. 15 to 21 show plan views and sectional views of variants of an orthosis joint.

FIG. 15 shows an orthosis joint in two views with a base body 10 as shown in FIG. 1. An orthosis rail serving as distal component 30 is mounted pivotably on the base body 10, such that a pivotability about the bearing point 13 is provided. In the right-hand view in FIG. 15, it will be seen that the distal component 30 forms, to both sides of the bearing point 13, support surfaces or shoulders 36, 37 which are assigned to the channels 163, 173 of the recesses 16, 17. It is thereby possible for functional elements, screwed into or otherwise secured in the recesses 16, 17, to be brought into direct contact with the support surfaces 36, 37 of the distal component 30.

FIG. 16 shows an illustrative embodiment in which only one receiving element 15 is screwed into the recess 17. As functional element 50, a limit stop is provided which is modifiable in position on the limit stop 50 via the inner thread 150 (not shown for reasons of clarity) and via a corresponding outer thread. It is thereby possible to adjust the maximum attainable pivot angle of the base body 10 relative to the distal component 30.

FIG. 17 shows a side view and a sectional view of a variant of the invention which corresponds to the structure in FIG. 10 with two limit stops 50 screwed in. It will be seen that both limit stops 50 rest on the support surfaces 36, 37 of the distal element 30, such that the joint does not permit relative movement.

FIG. 18 shows the variant of FIG. 12 with two screwed-in spring channels as receiving elements 14, 15. In addition, springs 60 as functional elements are arranged in each of the receiving elements 14, 15 and act on the support surfaces 36, 37 of the distal component 30 via balls 61. The pretensioning of the springs 60 can be adjusted via stoppers 142, 152 that can be screwed in.

FIG. 19 shows the variant of FIGS. 6 to 9 in the assembled state. The receiving element 14 serves to receive a spring 60, while the opposite receiving element 15 serves to receive a limit stop 50. It is thereby possible to permit a rotation about the bearing point 13 in the direction of the spring element 60, while the limit stop 50 blocks a pivoting movement of the base body 10 in the clockwise direction.

FIG. 20 shows the receiving elements 14, 15 in a longer version compared to FIG. 18. It will be seen from this that, by virtue of the modular structure, different springs 60 can be easily screwed into the base body 10 and can be fixed thereon. It is thereby possible to fit longer or stronger springs 60, if so desired by the patients.

FIG. 21 shows a combination of the embodiments of FIGS. 18 and 20, where the left-hand receiving element 14 is shorter than the right-hand receiving element, springs 60 as functional elements are arranged in both receiving elements 14, 15, such that it is possible, in different pivoting directions starting from the initial position shown, to apply different spring forces against pivoting.

ILLUSTRATIVE EMBODIMENTS

P1. An orthosis joint having a base body (10) which comprises a receptacle (12) for a proximal component (20), a bearing point (13) for a distal component (30) arranged pivotably on the base body (10), and limit stops or spring elements which act on the distal component (30), characterized in that at least one receiving element (14, 15), in or on which a functional element (50, 60, 70) interacting with the distal component (30) is arranged, is releasably secured to the base body (10).

P2. The orthosis joint as claimed in paragraph P1, characterized in that the receiving element (14, 15) is reversibly secured with a form fit to the base body (10).

P3. The orthosis joint as claimed in paragraph P1 or P2, characterized in that the receiving element (14, 15) is designed as a sleeve with at least one thread (140, 141, 150, 151).

P4. The orthosis joint as described in one of the preceding paragraphs, characterized in that the functional element (50, 60, 70) is designed as a spring, spring assembly, damper, sensor or limit stop, or a combination of these.

P5. The orthosis joint as described in one of the preceding paragraphs, characterized in that several functional elements (50, 60, 70) are arranged one behind another in series.

P6. The orthosis joint as described in one of the preceding paragraphs, characterized in that the functional element is designed as an inductive sensor (70), which detects a displacement path.

P7. The orthosis joint as described in one of the preceding paragraphs, characterized in that the receiving element (14, 15) is inserted in a recess (16, 17) in the base body (10), in which recess (16, 17) form-fit elements (160, 170) are arranged for securing the receiving element (14, 15), and in that a channel (163, 173) leads from the recess (16, 17) in the direction of the distal component (30).

P8. The orthosis joint as described in one of the preceding paragraphs, characterized in that the receptacle (12) is designed as a rail box.

P9. The orthosis joint as described in one of the preceding paragraphs, characterized in that the distal component (30) is designed as a rail, rail box, foot stirrup or foot support.

P10. The orthosis joint as described in one of the preceding paragraphs, characterized in that receiving elements (14, 15) are arranged on both sides of the bearing point (13).

P11. The orthosis joint as described in one of the preceding paragraphs, characterized in that the receiving element (14, 15) protrudes beyond the contour of the base body (10).

The invention claimed is:

1. An orthosis joint comprising:

a base body including a plurality of bores extending between a proximal side of the base body and a distal side of the base body, the base body being configured to be coupled to a proximal orthotic component on the proximal side of the base body;

a distal orthotic component pivotably coupled to the base body, the distal orthotic component being configured to pivot relative to the base body about a pivot axis;

a sleeve secured to one of the plurality of bores at the proximal side of the base body, the sleeve extending outward from the proximal side of the base body; and an integrated functional module positioned at least partially in the sleeve and in mechanical communication with the distal orthotic component, the integrated functional module including at least one of a limit stop, spring, damper, or sensor;

wherein the one bore extends through the base body on one side of the pivot axis and another of the plurality of bores extends through the base body on an opposite side of the pivot axis.

2. The orthosis joint of claim 1 wherein the sleeve is threadably secured to the one bore.

3. The orthosis joint of claim 1 wherein the sleeve includes threads on the inside of the sleeve.

4. The orthosis joint of claim 1 wherein a spring is positioned at least partially in the sleeve.

5. The orthosis joint of claim 1 comprising a stopper coupled to the sleeve and positioned to hold the limit stop, spring, damper, or sensor in the sleeve.

6. The orthosis joint of claim 1 wherein the sleeve is a first sleeve, the orthosis joint comprising:

a second sleeve secured to the another bore; and at least one of a limit stop, spring, damper, or sensor positioned at least partially in the second sleeve.

7. The orthosis joint of claim 1 comprising:

a slit positioned in the distal side of the base body;

wherein the slit is configured to receive the distal orthotic component; and wherein the plurality of bores are configured to open into the slit on the distal side of the base body.

8. The orthosis joint of claim 1 wherein the orthosis joint is an ankle joint.

9. An orthosis joint comprising:

a base body including a plurality of bores extending between a proximal side of the base body and a distal side of the base body, the base body being configured to be coupled to a proximal orthotic component on the proximal side of the base body;

a distal orthotic component pivotably coupled to the base body, the distal orthotic component being configured to pivot relative to the base body about a pivot axis; and an integrated functional module secured to one of the plurality of bores and extending outward from the proximal side of the base body, the integrated functional module including at least one of a limit stop, spring, damper, or sensor;

wherein the integrated functional module is configured to adjust or measure the pivoting movement of the distal orthotic component; and wherein the one bore extends through the base body on one side of the pivot axis and another of the plurality of bores extends through the base body on an opposite side of the pivot axis.

10. The orthosis joint of claim 9 wherein the integrated functional module is threadably secured to the one bore.

11. The orthosis joint of claim 9 wherein the integrated functional module includes a spring.

12. The orthosis joint of claim 11 wherein the integrated functional module includes a stopper configured to hold the spring in the integrated functional module.

13. The orthosis joint of claim 9 wherein the orthosis joint is an ankle joint.

14. A modular orthosis joint comprising:

the orthosis joint of claim 9 wherein the integrated functional module is a first integrated functional module; and a plurality of integrated functional modules including the first integrated functional module, each of the plurality of integrated functional modules being configured to be secured to at least one of the plurality of bores and extend outward from the proximal side of the base body, each of the plurality of integrated functional modules including at least one of a limit stop, spring, damper, or sensor.

15. The modular orthosis joint of claim 14 wherein the plurality of integrated functional modules include at least one of a spring module and at least one of a stop module.

16. A method of setting up the modular orthosis joint of claim 14, the method comprising:

securing the first integrated functional module to the one bore; and securing another of the plurality of integrated functional modules to the another bore.

17. An orthosis joint comprising:

a base body including a plurality of bores extending between a proximal side of the base body and a distal side of the base body, the base body being configured to be coupled to a proximal orthotic component on the proximal side of the base body;

a distal orthotic component pivotably coupled to the base body, the distal orthotic component being configured to pivot relative to the base body about a pivot axis;

an integrated functional module comprising at least two springs positioned in series and in mechanical communication with the distal orthotic component through one of the plurality of bores; and a sleeve secured to the one bore at the proximal side of the base body, wherein the sleeve extends outward from the proximal side of the base body, and wherein at least one of the at least two springs is positioned in the sleeve;

wherein the one bore extends through the base body on one side of the pivot axis and another of the plurality of bores extends through the base body on an opposite side of the pivot axis.

18. An orthosis joint comprising:

a base body including a first bore and a second bore both of which extend between a proximal side of the base body and a distal side of the base body, the base body being configured to be coupled to a proximal orthotic component on the proximal side of the base body;

a distal orthotic component pivotably coupled to the base body, the distal orthotic component being configured to pivot relative to the base body about a pivot axis;

a ball positioned in the first bore, the ball being in contact with the distal orthotic component;

a sleeve comprising at least one thread and secured to the base body, wherein the sleeve extends outward from the proximal side of the base body; and an integrated functional module comprising a spring positioned in the sleeve and extending in a proximal direction over the base body, the spring being positioned to bias the ball towards the distal orthotic component;

wherein the first bore extends through the base body on one side of the pivot axis and the second bore extends through the base body on an opposite side of the pivot axis.

19. The orthosis joint of claim 18 wherein the ball is a first ball and the spring is a first spring, the orthosis joint comprising:

a second ball positioned in the second bore, the second ball being in contact with the distal orthotic component; and a second spring positioned in the second bore, the second spring being positioned to bias the second ball towards the distal orthotic component.

* * * * *